(12) United States Patent
Hart et al.

(10) Patent No.: US 7,175,836 B1
(45) Date of Patent: *Feb. 13, 2007

(54) OIL CONTINUOUS PHASE COSMETIC EMULSIONS WITH CONJUGATED LINOLEIC ACID

(75) Inventors: Kelly Denise Hart, Cheshire, CT (US); Marcina Siciliano, New Haven, CT (US); Jeffrey William Rosevear, Wallingford, CT (US); Brian John Dobkowski, Milford, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/318,132

(22) Filed: Dec. 23, 2005

(51) Int. Cl.
*A61Q 17/04* (2006.01)
*A61K 8/00* (2006.01)
*A61K 8/06* (2006.01)
*A61K 31/19* (2006.01)

(52) U.S. Cl. .......................... 424/59; 424/60; 424/400; 424/401; 514/557; 514/844; 514/847; 514/937; 514/938; 514/969

(58) Field of Classification Search ................ 424/59, 424/60, 400, 401; 514/844, 847, 937, 938, 514/969, 557
See application file for complete search history.

(56) References Cited

U.S. PATENT DOCUMENTS

| | | |
|---|---|---|
| 5,422,371 A | 6/1995 | Liao et al. |
| 5,541,405 A | 7/1996 | Hassler, Jr. et al. |
| 5,723,139 A | 3/1998 | Granger et al. |
| 5,759,556 A | 6/1998 | Burger et al. |
| 5,972,359 A | 10/1999 | Sine et al. |
| 5,997,890 A | 12/1999 | Sine et al. |
| 6,019,990 A | 2/2000 | Remmereit |
| 6,171,581 B1 * | 1/2001 | Joshi et al. .................. 424/65 |
| 6,174,533 B1 | 1/2001 | SaNogueira, Jr. et al. |
| 6,287,553 B1 | 9/2001 | Alaluf et al. |
| 6,403,064 B1 | 6/2002 | Alaluf et al. |
| 6,524,598 B2 | 2/2003 | Sunkel et al. |
| 6,551,602 B1 | 4/2003 | Barrett et al. |
| 6,645,502 B2 * | 11/2003 | Sandewicz et al. .... 424/195.15 |
| 6,696,049 B2 | 2/2004 | Vatter et al. |
| 6,953,583 B1 | 10/2005 | Ghisalberti |
| 2003/0003068 A1 | 1/2003 | Mayes et al. |
| 2005/0118208 A1 | 6/2005 | Bewert et al. |
| 2005/0163730 A1 | 7/2005 | Rosevear et al. |

FOREIGN PATENT DOCUMENTS

| | | |
|---|---|---|
| EP | 0 742 005 B1 | 4/1996 |
| EP | 0 803 247 B1 | 4/1997 |
| FR | 2 780 886 | 7/1998 |
| WO | 98/13020 | 4/1998 |
| WO | 99/26588 | 6/1999 |
| WO | 01/08650 A1 | 2/2001 |

* cited by examiner

*Primary Examiner*—Shelley A. Dodson
(74) *Attorney, Agent, or Firm*—Milton L. Honig

(57) ABSTRACT

A cosmetic water-in-oil composition is provided which includes a water-in-oil emulsifying silicone surfactant, crosslinked silicone elastomer and conjugated linoleic acid. The conjugated linoleic acid functions to improve radiance on facial surfaces to which the composition is topically applied.

8 Claims, No Drawings

OIL CONTINUOUS PHASE COSMETIC EMULSIONS WITH CONJUGATED LINOLEIC ACID

BACKGROUND OF THE INVENTION

1. Field of the Invention

The invention concerns a cosmetic emulsion composition formulated to improve the appearance of brightness and radiance when applied to a person's face.

2. The Related Art

First impressions are visual. Vitality is evidenced by a person's face. Important elements reflecting vitality are those of facial brightness and radiance. These attributes can be enhanced by topical application of appropriate cosmetic compositions.

Cosmetics can be formulated to manipulate light transmission. Some types of components may reflect light back toward the source. Other additives may achieve a soft focus effect. Here the incoming light is distorted by scattering (lensing). In this mechanism the scattering components operate as lenses to bend and twist light into a variety of directions.

U.S. Pat. No. 5,997,890 (Sine et al.), U.S. Pat. No. 5,972,359 (Sine et al.), and U.S. Pat. No. 6,174,533 B1 (SaNogueira, Jr.) are all based on using the soft focus effect to provide good coverage of skin imperfections. The solution proposed by these documents is the use of a metal oxide with a refractive index of at least about 2 and a neat primary particle size of from about 100 to about 300 nm. Preferred particulates are titanium dioxide, zirconium oxide and zinc oxide.

US Patent publication no. 2005/0163730 A1 (Rosevear et al.) describes cosmetic compositions that include a crosslinked silicone elastomer, a zinc oxide and light reflecting inorganic material of platelet-shaped particles. The system is said to achieve soft focus and impart radiance to the skin.

Advances on achieving a matte effect as seen in the aforementioned literature have been achieved through manipulation of inorganic pigments. Unfortunately pigment particles can give rise to problems, especially at increased concentration levels. These problems include degradation of skinfeel and formulation phase instability. Therefore, new approaches have been sought to imparting vitality through improved brightness and radiance.

SUMMARY OF THE INVENTION

A cosmetic composition is provided which is a water-in-oil emulsion including:
  (i) from about 0.1 to about 30% by weight of a water-in-oil emulsifying silicone surfactant;
  (ii) from about 0.01 to about 30% by weight of a crosslinked silicone elastomer; and
  (iii) from 0.2 to 1.5% of a conjugated linoleic acid.

DETAILED DESCRIPTION OF THE INVENTION

Now it has been found that a water-in-oil cosmetic composition containing conjugated linoleic acid can impart a much improved brightness and radiance when topically applied to the face. It was surprising that the conjugated linoleic acids have an effect on improving brightness and radiance. Further, formulation with crosslinked silicone elastomers is believed to enhance these effects.

Conjugated Linoleic Acid

Conjugated linoleic acid (hereinafter referred to also as CLA) comprises a group of positional and geometric isomers of linoleic acid in which various configurations of cis and trans double bonds at positions (6,8), (7,9), (8,10), (9,11), (10,12) or (11,13) are possible. Thus, twenty-four different isomers of CLA exist.

The invention also includes derivatives of the free acid which thus comprise conjugated linoleic acid moieties. Preferable derivatives include those derived from substitution of the carboxyl group of the acid, such as esters (e.g. retinyl esters, triglyceride esters, monoglyceride esters, diglyceride esters, phosphoesters), amides (e.g. ceramide derivatives), salts (e.g. alkali metal and alkali earth metal salts, ammonium salts); and/or those derived from substitution of the C18 carbon chain, such as alpha hydroxy and/or beta hydroxy derivatives.

In the case of triglyceride ester derivatives, all positional isomers of CLA substituents on the glycerol backbone are included. The triglycerides must contain at least one CLA moiety. For example, of the three esterifiable positions on the glycerol backbone, the 1 and 2 positions may be esterified with CLA and by another lipid at position 3 or as an alternative, the glycerol backbone could be esterified by CLA at the 1 and 3 positions with another lipid at position 2.

Wherever the term "conjugated linoleic acid" or "CLA" is used in this specification it is to be understood that the derivatives thereof comprising CLA moieties are also included. "CLA moieties" refers to CLA fatty acyl portion(s) of a CLA derivative.

The isomers of greatest interest in the present cosmetic compositions are cis 9, trans11-linoleic acid and trans10, cis12-linoleic acid. Hereinafter the term "9,11-linoleic" or "10,12-linoleic" shall mean preferentially these two main isomers, but will include lesser amounts of the remaining isomers, particularly when obtained or derived from a natural source.

In accordance with the present invention, 9,11-linoleic acid and 10,12-linoleic acid are formulated into cosmetic preparations either as the free acid, as individual chemical derivatives, or as combinations of free acid and derivative.

By "c9, t11 and t10, c12 isomer enriched CLA" is meant that at least 30% by weight of the total CLA (and/or CLA moieties) present in the composition is in the form of the cis 9, trans 11 and trans 10, cis 12 isomers. Preferably, at least 40%, most preferably at least 50%, by weight of the total CLA and/or CLA moieties present in the composition, is in the form of the aforementioned isomers.

Amount of the CLA present in emulsions of this invention may range from 0.2 to 1.5% by weight of the composition. More preferably the amount is from 0.5% to 1.2% and even more preferably from 0.8 to 1%.

Mixed isomers of CLA are prepared by high temperature alkali treatment of Safflower oil, generating CLA with equal amounts of the c9, t11 and t10, c12 CLA isomers. CLA enriched in the c9, t11 CLA is separated from the mix by selective esterification with lauryl alcohol using *Geotrichum Candidum* as a catalyst. The enriched c9, t11 CLA is hydrolyzed and converted to the triglyceride. After the esterification step and separation the remaining CLA free acids are enriched in t10, c12 CLA.

Commercially CLA is available as Clarinol® A-80 and A-95 from Loders-Croklaan, Channahon, Ill. and Neobee® CLA 80 and 90 from Stepan, North Field, Ill.

Water-in-Oil Surfactant

A wide variety of silicone surfactants are useful herein. These silicones are typically organically modified organopolysiloxanes such as dimethicone copolyols.

Nonlimiting examples of dimethicone copolyols and other silicone surfactants useful herein include polydimethylsiloxane polyether copolymers with pendant polyethylene oxide side chains, polydimethylsiloxane polyether copolymers with pendant polypropylene oxide side chains, polydimethylsiloxane polyether copolymers with pendant mixed polyethylene oxide and polypropylene oxide side chains, polydimethylsiloxane polyether copolymers with pendant mixed poly(ethylene)(propylene)oxide side chains, polydimethylsiloxane polyether copolymers with pendant organobetaine side chains, polydimethylsiloxane polyether copolymers with pendant carboxylate side chains, polydimethylsiloxane polyether copolymers with pendant quaternary ammonium side chains; and also further modifications of the preceding copolymers containing pendant C2–C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this latter material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate sold under the tradename ABIL® WS-08 (also available from Goldschmidt). Other nonlimiting examples of dimethicone copolyols include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, dimethicone copolyol sulfosuccinate and dimethicone copolyol stearate. Most preferred is PEG-10 Dimethicone available from Shin Etsu.

Amounts of the silicone surfactant may range from about 0.1 to about 30%, preferably from about 1 to about 10%, optimally from about 1.5 to about 5% by weight of the composition.

Crosslinked Silicone Elastomer

A component of the present invention is a crosslinked silicone (organopolysiloxane) elastomer. No specific restriction exists as to the type of curable organopolysiloxane composition that can serve as starting material for the crosslinked silicone elastomer. Examples in this respect are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl terminated diorganopolysiloxane and SiH-containing diorganopolysiloxane; condensation-curing organopolysiloxane compositions which cure in the presence of an organotin compound or a titanate ester, by a condensation reaction between a hydroxyl terminated diorganopolysiloxane and a hydrolyzable organosilane (this condensation reaction is exemplified by dehydration, alcohol-liberating, oxime-liberating, amine-liberating, amide-liberating, carboxyl-liberating, and ketone-liberating reactions); peroxide-curing organopolysiloxane compositions which thermally cure in the presence of an organoperoxide catalyst; and organopolysiloxane compositions which are cured by high-energy radiation, such as by gamma-rays, ultraviolet radiation, or electron beams.

Addition reaction-curing organopolysiloxane compositions are preferred for their rapid curing rates and excellent uniformity of curing. A particularly preferred addition reaction-curing organopolysiloxane composition is prepared from:

(A) an organopolysiloxane having at least 2 lower alkenyl groups in each molecule;

(B) an organopolysiloxane having at least 2 silicon-bonded hydrogen atoms in each molecule; and (C) a platinum-type catalyst.

The crosslinked siloxane elastomer of the present invention may either be an emulsifying or non-emulsifying crosslinked organopolysiloxane elastomer or combinations thereof. The term "non-emulsifying," as used herein, defines crosslinked organopolysiloxane elastomer from which polyoxyalkylene units are absent. The term "emulsifying," as used herein, means crosslinked organopolysiloxane elastomer having at least one polyoxyalkylene (e.g., polyoxyethylene or polyoxypropylene) unit.

Particularly useful emulsifying elastomers are polyoxyalkylene-modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin.

Preferred silicone elastomers are organopolysiloxane compositions available under the INCI names of dimethicone/vinyl dimethicone crosspolymer, dimethicone crosspolymer and Polysilicone-11. Ordinarily these materials are provided as a 1–30% crosslinked silicone elastomer dissolved or suspended in a dimethicone fluid (usually cyclomethicone). For purposes of definition "crosslinked silicone elastomer" refers to the elastomer alone rather than the total commercial compositions which also include a solvent (eg dimethicone) carrier.

Dimethicone/vinyl dimethicone crosspolymers and dimethicone crosspolymers are available from a variety of suppliers including Dow Corning (9040, 9041, 9045, 9506 and 9509), General Electric (SFE 839), Shin Etsu (KSG-15, 16, 18 [dimethicone/phenyl vinyl dimethicone crosspolymer]), and Grant Industries (Gransil™ line of materials), and lauryl dimethicone/vinyl dimethicone crosspolymers supplied by Shin Etsu (e.g, KSG-31, KSG-32, KSG-41, KSG-42, KSG-43, and KSG-44).

Other suitable commercially available silicone elastomer powders include vinyl dimethicone/methicone silesquioxane crosspolymers from Shin-Etsu sold as KSP-100, KSP-101, KSP-102, KSP-103, KSP-104, KSP-105, and hybrid silicone powders that contain a fluoroalkyl group or a phenyl group sold by Shin-Etsu as respectively KSP-200 and KSP-300.

The crosslinked silicone elastomers of the present invention may range in concentration from about 0.01 to about 30%, preferably from about 0.1 to about 10%, optimally from about 0.5 to about 2% by weight of the cosmetic composition. These weight values exclude any solvent such as cyclomethicone found in commercial "elastomer" silicones such as the Dow Corning products 9040 and 9045. For instance, the amount of crosslinked silicone elastomer in 9040 and 9045 is between 12 and 13% by weight.

Most preferred as the silicone elastomer is 9045 which has a D5 cyclomethicone swelled elastomer particle size (based on volume and calculated as spherical particles) which averages about 38 micron, and may range from about 25 to about 55 micron.

Carrier for Silicone Elastomer

The compositions of the present invention may include from about 1% to about 80%, by weight of the composition, of a suitable carrier for the crosslinked organopolysiloxane elastomer component described above. The carrier, when combined with the cross-linked organopolysiloxane elastomer particles serves to suspend and swell the elastomer particles to provide an elastic, gel-like network or matrix. The carrier for the crosslinked siloxane elastomer is liquid under ambient conditions, and preferably has a low viscosity to provide for improved spreading on the skin.

Concentrations of the carrier may range from about 5% to about 60%, more preferably from about 5% to about 40%, by weight of the composition.

These liquid carriers may be organic, silicone-containing or fluorine-containing, volatile or non-volatile, polar or non-polar, provided that the liquid carrier forms a solution or other homogeneous liquid or liquid dispersion with the selected cross-linked siloxane elastomer at the selected siloxane elastomer concentration at a temperature of from about 28° C. to about 250° C., preferably from about 28° C. to about 78° C. The term "non-polar" typically means that the material has a solubility parameter below about 6.5 $(cal/cm^3)^{0.5}$.

The non-polar, volatile oil tends to impart highly desirable aesthetic properties to the compositions of the present invention. Consequently, the non-polar, volatile oils are preferably utilized at a fairly high level. Non-polar, volatile oils particularly useful in the present invention are silicone oils; hydrocarbons; and mixtures thereof. Examples of preferred non-polar, volatile hydrocarbons include polydecanes such as isododecane and isodecane (e.g., Permethyl-99A which is available from Presperse Inc.) and the C7–C8 through C12–C15 isoparaffins (such as the Isopar Series available from Exxon Chemicals). Particularly preferred volatile silicone oils are cyclic volatile silicones wherein the repeating unit ranges from about 3 to about 5; and linear silicones wherein the repeating unit ranges from about 1 to about 7. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids, GE 7207 and 7158 (commercially available from G.E. Silicones) and SWS-03314 (commercially available from SWS Silicones Corp.

Dispersed Aqueous Phase

The compositions of the present invention comprise from about 25% to about 90%, more preferably from about 30% to about 75%, and even more preferably from about 45% to about 60% of a dispersed aqueous phase. In emulsion technology, the term "dispersed phase" means that the phase exists as small particles or droplets suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, sunscreening agents and colorants.

Optional Components

The composition of the present invention may contain a variety of other ingredients that are conventionally used in given product types provided that they do not unacceptably alter the benefits for the invention.

The ingredients, when incorporated into the composition, should be suitable for use in contact with human keratinous tissue without undue toxicity, incompatibility, instability, allergic response, and the like within the scope of sound judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g. clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents, skin conditioning agents, skin soothing and/or healing agents and derivatives, skin treating agents, thickeners, and vitamins and derivatives thereof.

In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

The compositions of the present invention may further comprise a safe and effective amount of one or more anti-wrinkle or anti-atrophy actives. Exemplary actives include hydroxy acids (e.g., salicylic acid, glycolic acid), keto acids (e.g. pyruvic acid), ascorbic acid (vitamin C), phytic acid, lysophosphatidic acid, flavonoids (e.g., isoflavones, flavones, etc), stilbenes, cinnamates, resveratrol, kinetin, zeatin, dimethylaminoethanol, eugenyl glycoside, N-actyl glucosamine esters, ergosterol or ergosterol glycosides, peptides from natural sources (e.g. soy peptides), salts of sugar acids (e.g. Mn gluconate), and retinoids (e.g. retinol, retinyl palmitate) which enhance the keratinous tissue appearance benefits of the present invention, especially in regulating keratinous tissue condition, and other vitamin B compounds (e.g, thiamine (vitamin B1), panthothenic acid (vitamin B5), carnitine (vitamin Bt), riboflavin (vitamin B2), and their derivatives and salts (e.g. HCl salts or calcium salts)).

The compositions of the present invention may include an anti-oxidant/radical scavenger. The anti-oxidant/radical scavenger is especially useful for providing protection against UV radiation that can cause increased scaling or texture changes in the stratum coneum and against other environmental agents, which can cause skin damage.

A safe and effective amount of an anti-oxidant/radical scavenger may be added in amounts from about 0.01% to about 10%, more preferably from about 0.1% to about 5% by weight of the composition.

Anti-oxidants/radical scavengers such as ascorbic acid (vitamin C) and its salts, ascorbyl esters of fatty acids, ascorbic acid derivatives (e.g. magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolor®), amines (e.g. N,N-diethylhydroxylamine, amino-guanidine), nordihydroguaiaretic acid, bioflavonoids, amino acids, silymarin, tea extracts, and grape skin/seed extracts may be used. Preferred anti-oxidants/radical scavengers are selected from esters of tocopherol, more preferably tocopherol acetate.

The compositions of the present invention may optionally comprise a flavonoid compound. Flavonoids are disclosed in U.S. Pat. Nos. 5,686,082 and 5,686,367 herein incorporated by reference. Examples of flavonoids particularly suitable flavones, isoflavones, coumarins, chromones, discoumarols, chromanones, chromanols, isomers (e.g. cis/trans isomers) thereof, and mixtures thereof.

Preferred for use are flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy), and mixtures thereof. Flavonoid compounds useful herein are commercially available from a number of sources, e.g., Indofine Chemical Company, Inc., Stearloids, Inc., and Aldrich Chemical Company, Inc. The herein described flavonoid compounds are preferably present in from about 0.01% to about 20%, more preferably from about 0.1% to about 10%, and even more preferably from about 0.5% to about 5% by weight.

A safe and effective amount of an anti-inflammatory agent may be added to the compositions of the present invention, preferably from about 0.01% to about 10%, more preferably from about 0.5% to about 5% by weight of the composition. The anti-inflammatory agent enhances the skin appearance benefits of the present invention, e.g. such agents contribute to a more uniform and acceptable skin tone or color.

Steroidal anti-inflammatory agents, include but are not limited to, corticosteroids such as hydrocortisone. A second class of anti-inflammatory agents includes the nonsteroidal anti-inflammatory agents. Specific non-steroidal anti-inflammatory agents include but are not limited to, salicylate, ibuprofen, flufenamic acid, etofenamate, aspirin, and mixtures thereof.

Additional anti-inflammatory agents useful herein include allantoin and compounds of the Licorice (the plant genus/species *Glycyrrhiza glabra*) family, including glycyrrhetic acid, glycyrrhizic acid, and derivatives thereof (e.g. salts and esters).

The compositions may also comprise a safe and effective amount of an anti-cellulite agent. Suitable agents may include, but are not limited to, xanthine compounds (e.g. caffeine, theophylline, theobromine, and aminophylline).

The compositions may comprise a tanning active. When present, it is preferable that the compositions comprise from about 0.1% to about 20%, more preferably from about 2% to about 7% by weight of the composition. A preferred tanning active is dihydroxyacetone.

The compositions may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include niacinamide, kojic acid, arbutin, tranexamic acid, placental extract, ascorbic acid and derivatives thereof (e.g. magnesium ascorbyl phosphate, sodium ascorbyl phosphate, ascorbyl glucoside, and ascorbyl tetraisopalmitates). Other skin lightening materials suitable for use herein include Actiwhite® (Cognis), Emblica® (Rona), Azeloglicina (Sinerga) and extracts (e.g. mulberry extract).

The compositions may comprise an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and even more preferably from about 0.05% to about 2% by weight of the composition.

Preferred examples of actives include those selected from the group consisting of salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cystein, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, ciclopirox, lidocaine hydrochloride, clotrimazole, climbazole, miconazole, ketoconazole, neocycin sulfate, and mixtures thereof.

The compositions of the subject invention may optionally contain a sunscreen active. As used herein, "sunscreen active" includes both sunscreen agents and physical sunblocks. Suitable sunscreen actives may be organic or inorganic.

Particularly suitable sunscreen agents are 2-ethylhexyl-p-methoxycinnamate (commercially available as PARSOL MCX), 4,4'-t-butyl methoxydibenzoylmethane (commercially available as PARSOL 1789), 2-hydroxy-4-methoxybenzophenone, octyidimethyl-p-aminobenzoic acid, digalloyltrioleate, 2,2-dihydroxy-4-methoxybenzophenone, ethyl-4-(bis(hydroxy-propyl)) aminobenzoate, 2-ethylhexyl-2-cyano-3,3-diphenylacrylate, 2-ethylhexyl-salicylate, glycerol-p-aminobenzoate, 3,4,5-trimethylcyclohexylsalicylate, methylanthranilate, p-dimethyl-aminobenzoic acid or aminobenzoate, 2-ethylhexyl-p-dimethyl-aminobenzoate, 2-phenylbenzimidazole-5-sulfonic acid, 2-(p-dimethylaminophenyl)-5-sulfonic benzoxazoic acid, octocrylene, zinc oxide, titanium dioxide, and mixtures of these compounds.

A safe and effective amount of the sunscreen active is used, typically from about 1% to about 20%, more typically from about 2% to about 10% by weight of the composition.

Exact amounts will vary depending upon the sunscreen chosen and the desired Sun Protection Factor (SPF).

The compositions may comprise a conditioning agent selected from the group consisting of humectants, moisturizers, or skin conditioners. A variety of these materials can be employed and each can be present at a level of from about 0.01% to about 40%, more preferably from about 0.1% to about 30%, and even more preferably from about 0.5% to about 15% by weight of the composition. These materials include, but are not limited to, guanidine; urea; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy compounds such as sorbitol, mannitol, glycerol, hexanetriol, butanetriol, propylene glycol, butylene glycol and hexylene glycol; polyethylene glycols; sugars and starch derivatives (e.g. alkoxylated glucose, fructose, sucrose, trehalose); hyaluronic acid; lactamide monoethanolamine; acetamide monoethanolamine; sucrose polyester; petrolatum; and mixtures thereof.

Preferably, the conditioning agent is selected from the group consisting of glycerol, urea, hydroxyethyl urea, petrolatum, sucrose polyester, and combinations thereof.

The compositions can comprise one or more thickening agents, preferably from about 0.05% to about 10%, more preferably from about 0.1% to about 5%, and even more preferably from about 0.25% to about 4%, by weight for the composition. Nonlimiting classes of thickening agents include those selected from the group consisting of:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon—carbon double bonds and is derived from a polyhydric alcohol Examples of commercially available carboxylic acid polymers useful herein include the Carbomers, which are homopolymers of acrylic acid crosslinked with allyl ethers of sucrose or pentaerytritol. The Carbomers, are available as the Carbopol® 900 series from Noveon Corporation (e.g. Carbopol® 954). In addition, other suitable carboxylic acid polymeric agents include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytriotol. These copolymers are known as Acrylates/$C_{10-30}$ Alkyl Acrylate Crosspolymers and are commercially available as Carbopol® 1342, Carbopol® 1382, Ultrez® 21, Pemulen® TR-1, and Pemulen® TR-2, from Noveon Corporation.

b. Taurate Polymers

The compositions of the present invention can optionally comprise crosslinked taurate polymers useful as thickeners or gelling agents including anionic, cationic and nonionic polymers. Examples include Hydroxyethyl Acrylate/Sodium Acryloyldimethyl Taurate (e.g. Simulgel® NS and INS 100), Acrylate/Sodium Acryloyldimethyl Taurate (e.g. Simulgel® EG), Sodium Acryloyidimethyl Taurate (e.g. Simulgel® 800) and Ammonium Acryloyldimethyl Taurate/Vinyl Pyrrolidone (e.g. Aristoflex® AVC).

c. Polyacrylamide Polymers

The compositions of the present invention can optionally comprise polyacrylamide polymers, especially nonionic polyacrylamide polymers including substituted branched or unbranched polymers. Preferred among these polyacrylamide polymers is the nonionic polymer given the CTFA designation polyacrylamide and isoparaffin and laureth-7, available under the tradename Sepigel® 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

d. Polysaccharides

A wide variety of polysaccharides are useful herein. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof.

e. Gums and Clays

Other thickening and gelling agents useful herein include materials that are primarily derived from natural sources. Nonlimiting examples include materials selected from the group consisting of acacia, aga, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, laponite, bentonite, hyaluronic acid, hydrated silica, hydroxypropyl chitosan, hydroxypropyl guar, karaya gum, kelp, locust bean gum, natto gum, potassium carrageenan, propylene glycol alginate, sclerotium gum, sodium carboxymethyl dextran, sodium carrageenan, tragacanth gum, xanthan gum, and mixtures thereof.

The compositions of the present invention may contain one or more particulate materials. Nonlimiting examples of particulate materials include colored and uncolored pigments, interference pigments, inorganic powders, organic powders, composite powders, optical brightener particles, and combinations thereof. Particulate materials may be present from about 0.01% to about 20%, more preferably from about 0.05% to about 10%, still more preferably from about 0.1% to about 5%, by weight of the composition.

Particulate materials useful herein include but are not limited to bismuth oxychloride, sericite, mica, mica treated with barium sulfate or titanium dioxide, zeolite, kaolin, silica, boron nitride, lauroyl lysine, nylon, talc, styrene, polystyrene, ethylene/acrylic acid copolymer, aluminum oxide, silicone resin, barium sulfate, calcium carbonate, cellulose acetate, PTFE, polymethyl methacrylate, starch, modified starches, silk, glass, and mixtures thereof. Preferred organic powders/fillers include polymeric particles chosen from the methylsilsesquioxane resin microspheres such as those sold by Toshiba Silicone under the name Tospearl 145A; microspheres of polymethylmethacrylates such as those sold by Seppic under the name Micropearl M 100; the spherical particles of crosslinked polydimethylsuloxanes, especially such as those sold by Dow Corning Toray Silicone under the name Trefil E 506C or Trefil E 505C; spherical particles of polyamide and more specifically Nylon 12, especially such as those sold by Atochem under the name Orgasol 2002N Nat C05; polystyrene microspheres such as those sold by Dyno Particles under the name Dynospheres; ethylene acrylate copolymer sold by Kobo under the name FloBead EA209; PTFE; polypropylene; aluminum starch octenylsuccinate such as sold by National Starch under the name Dry Flo; microspheres of polyethylene such as those sold by Equistar under the name of Microthene FN510-00; silicone resin; platelet shaped powder made from L-lauroyl lysine, and mixtures thereof. Especially preferred are spherical powders with an average primary particle size from 0.1 to 75 microns, preferably from 0.2 to 30 microns.

Also useful herein are interference pigments. Interference pigments, are defined as thin platelike layered particles having two or more layers of controlled thickness with different refractive indices that yield a characteristic reflected color from the interference of typically two, but occasionally more, light reflections, forming different layers of the platelike particle. The most common examples of interference pigments are micas layered with about 50–300 nm films of TiO2, Fe2O3, silica, tin oxide, and/or Cr2O3. Such pigments are often pearlescent. Useful interference pigments are available commercially from a wide variety of suppliers, for example, Rona (Timiron® and Cichrona®, Presperse (Flonac®), Englehard (Duochrome®), Kobo (SK45-R and SK45-G), BASF (Sicopearls) and Eckart (e.g. Prestige Silk Red). Especially preferred are interference pigments with smaller particle sizes, with an average diameter of individual particles less than about 75 microns in the longest direction, preferably with an average diameter less than about 50 microns.

Other pigments useful in the present invention provide color primarily through selective absorption of specific wavelengths of visible light, and include inorganic pigments, organic pigments and combinations thereof. Examples of useful inorganic pigments include iron oxides, ferric ammonium ferrocyanide, manganese violet, ultramarine blue, and Chrome oxide. Organic pigments can include natural colorants and synthetic monomeric and polymeric colorants. An example is phthalocyanine blue and green pigment. Also useful are lakes, primary FD&C or D&C lakes and blends thereof. Also useful are encapsulated soluble or insoluble dyes and other colorants. Inorganic white or uncolored pigments useful in the present invention, for example TiO2, ZnO, or $ZrO_2$, are commercially available from a number of sources.

Preferred colored or uncolored non-interference-type pigments have a primary average particle size of from about 10 nm to about 100,000 nm, more preferably from about 20 nm to about 5,000 nm, even more preferably from about 20 nm to about 1000 nm. Mixtures of the same or different pigment/powder having different particle sizes are also useful herein (e.g., incorporating a TiO2 having a primary particle size of from about 100 nm to about 400 nm with a TiO2 having a primary particle size of from about 10 nm to about 50 nm).

The pigments/powders can be surface treated to provide added stability of color and/or for ease of formulation. Non-limiting examples of suitable coating materials include silicones, lecithin, amino acids, metal soaps, polyethylene and collagen. These surface treatments may be hydrophobic or hydrophilic, with hydrophobically treatments being preferred.

The topical compositions of the subject invention include but are not limited to lotions, milks, mousses, serums, sprays, aerosols, foams, sticks, pencils, gels, creams and ointments. The compositions may also be applied via a woven or nonwoven synthetic and/or natural fibered textile (wipe or towelette).

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLES I–V

A moisturizing skin cream/lotion is prepared by conventional methods from the following components.

| Component | I | II | III | IV | V |
|---|---|---|---|---|---|
| Phase A | | | | | |
| Water | Qs | Qs | Qs | Qs | Qs |
| Allantoin | 0.2000 | 0.2000 | 0.2000 | 0.2000 | 0.2000 |
| Disodium EDTA | 0.1000 | 0.1000 | 0.1000 | 0.1000 | 0.1000 |
| Ethyl Paraben | 0.2000 | 0.2000 | 0.2000 | 0.2000 | 0.2000 |
| Propyl Paraben | 0.1000 | 0.1000 | 0.1000 | 0.1000 | 0.1000 |
| Butylated Hydroxytoluene | 0.0150 | 0.0150 | 0.0150 | 0.0150 | 0.0150 |
| Panthenol | 1.0000 | 0.5000 | 1.0000 | 1.0000 | 1.0000 |
| Glycerin | 7.5000 | 10.000 | 15.000 | 7.5000 | 5.0000 |
| N-Undecylenoyl-L-Phenylalanine | 2.0000 | 0.5000 | 1.0000 | 4.0000 | 1.0000 |
| Hexamidine Isethionate | 0.0000 | 0.1000 | 0.1000 | 0.0000 | 1.0000 |
| Niacinamide | 0 | 3.5000 | 5.0000 | 2.0000 | 2.0000 |
| Palmitoyl-Pentapeptide (1) | 0 | 0 | 0 | 0.0004 | 0.0003 |
| Phenylbenzimidazole Sulfonic Acid | 0 | 0 | 0 | 0 | 1.0000 |
| Benzyl Alcohol | 0.2500 | 0.2500 | 0.2500 | 0.2500 | 0.2500 |
| Triethanolamine | 0.8000 | 0.2000 | 0.4000 | 1.6000 | 1.0000 |
| Green Tea Extract | 1.0000 | 1.0000 | 1.0000 | 1.0000 | 1.0000 |
| N-Acetyl Glucosamine | 0.0000 | 5.0000 | 2.0000 | 1.0000 | 5.0000 |
| Sodium Metabisulfite | 0.1000 | 0.1000 | 0.1000 | 0.1000 | 0.1000 |
| Phase B | | | | | |
| Cyclopentasiloxane | 15.000 | 15.000 | 18.000 | 15.000 | 15.000 |
| Titanium Dioxide | 0.5000 | 0.5000 | 0.7500 | 0.5000 | 0.5000 |
| Phase C | | | | | |
| C12–C15 Alkyl Benzoate | 1.5000 | 0 | 0 | 1.5000 | 1.5000 |
| Dipalmitoyl Hydroxyproline | 0 | 1.0000 | 0 | 0 | 1.0000 |
| Salicylic Acid | 1.5 | 0 | 0 | 0 | 0 |
| PPG-15 Stearyl Ether | 4 | 0 | 0 | 0 | 0 |
| Vitamin E Acetate | 0.5000 | 0 | 1.0000 | 0.5000 | 0.5000 |
| Retinyl Propionate | 2.0000 | 0 | 0 | 0.2000 | 0.2000 |
| Phytosterol | 0.0000 | 1.0000 | 1.0000 | 5.0000 | 3.0000 |
| Phase D | | | | | |
| KSG-21 Silicone Elastomer (2) | 20.5000 | 26.0000 | 26.0000 | 20.5000 | 20.5000 |
| Silicone Non-Emulsifying Elastomer | 0 | 1.0000 | 1.0000 | 0 | 0.5000 |
| Abil EM-97 Dimethicone Copolyol (3) | 0.5000 | 0 | 0 | 0.5000 | 0.5000 |
| Clarinol A-80 ® | 0.5000 | 0.5000 | 1.0000 | 1.0000 | 1.5000 |

-continued

| Component | I | II | III | IV | V |
|---|---|---|---|---|---|
| Polymethylsilsesquioxane | 2.5000 | 2.5000 | 2.0000 | 2.5000 | 2.5000 |
| Fragrance | 0.2000 | 0.2000 | 0.2000 | 0.2000 | 0.2000 |

(1) palmitoyl-pentapeptide = palmitoyl-lysine-threonine-threonine-lysine-serine available from Sederma.
(2) KSG-21, an emulsifying silicone elastomer available from Shin Etsu
(3) Abil EM-97 available from Goldschmidt Chemical Corporation In a suitable vessel, the Phase A components are blended together with a suitable mixer (e.g. Tekmar model RW20DZM) and mixing is continued until all of the components are dissolved. Then, the Phase B components are blended together in a suitable vessel and are milled using a suitable mill (e.g. Tekmar RW-20) for about 5 minutes. The Phase C components are then added to the Phase B mixture with mixing. Then, the Phase D components are added to the mixture of Phases B and C and the resulting combination of Phase B, C, and D components is then mixed using a suitable mixer (e.g. Tekmar RW-20) for about 1 hour. Then, Phase A is slowly added to the mixture of Phases B, C and D with mixing. The resulting mixture is continually mixed until the product is uniform. The resulting product is then milled for about 5 minutes using an appropriate mill (e.g. Tekmar T-25).

EXAMPLES VI–X

Another series of facial skin creams according to the present invention is prepared in a manner similar to that reported for Example I–V. The creams have the following components.

| Component | VI | VII | VIII | IX | X |
|---|---|---|---|---|---|
| Phase A | | | | | |
| Deionized Water | Qs | Qs | Qs | Qs | Qs |
| Phase B (Surfactant Network) | | | | | |
| NET-WO (PEG-10 Dimethicone & Disteardimonium Hectorite & Cyclopentasiloxane | 2.8000 | 1.8000 | 1.8000 | 0.8000 | 2.8000 |
| KF 6017 (PEG-10 Dimethicone) | 2.6000 | 1.6000 | 1.8000 | 0.8000 | 2.8000 |
| Phase C (Humectant/Emollient) | | | | | |
| Glycerin | 10.0000 | 12.0000 | 12.0000 | 14.0000 | 9.0000 |
| Caprylic/Capric Triglycerides | 5.0000 | 3.0000 | 2.0000 | 2.0000 | 2.0000 |
| Phase D (Sunscreen) | | | | | |
| Parsol MCX (Ethylhexyl Methoxycinnamate) | 6.0000 | 6.0000 | 4.0000 | 4.0000 | 4.0000 |
| Phase E (Silicone) | | | | | |
| DC 9045 (Dimethicone Crosspolymer and Cyclopentasiloxane) | 20.0000 | 26.0000 | 26.0000 | 20.0000 | 16.0000 |
| Phase F (Visual Enhancement) | | | | | |
| Z-COTE HP1 (Zinc Oxide and Triethoxycaprylsilane) | 2.0000 | 2.0000 | 4.0000 | 4.0000 | 3.0000 |

-continued

| Component | VI | VII | VIII | IX | X |
|---|---|---|---|---|---|
| Phase G | | | | | |
| Clarinol ® A-80 (Conjugated Linoleic Acid) | 0.500 | 0.500 | 1.0000 | 1.0000 | 1.3000 |
| Herbal Extracts/Nutrients* | 4.3000 | 4.3000 | 4.3000 | 4.3000 | 4.3000 |
| Phase H (Fragrance/Anti-Oxidant/Preservative) | | | | | |
| Fragrance | 0.8500 | 0.3500 | 0.3500 | 0.3500 | 0.8500 |
| Disodium EDTA | 0.2500 | 0.0500 | 0.0500 | 0.2500 | 0.3500 |
| Glydant Plus Liquid (DMDM Hydantoin and Iodopropynyl Butylcarbamate) | 0.2000 | 0.2000 | 0.1000 | 0.1000 | 0.1000 |

*Includes: Vitamin E Acetate, Vitamin A Palmitate, Ceramide 1, 3 and 6, Bisabolol, Borage Oil, Coriander Seed Oil, Sodium Lactate, Sodium Ascorbyl Phosphate, Betula Alba Extract (White Birch), DL-Panthenol, Sodium PCA (50%), Hydrolyzed Milk protein, Pomegranate Extract, Cholesterol and Stearic Acid.

EXAMPLE XI

An Expert Facial Evaluation study was undertaken to measure the effects of an oil continuous emulsion formulated with four different levels of CLA in combination with a silicone elastomer. The following Table outlines the four compositions (A–D) employed for this study.

| | Composition (Weight %) | | | |
|---|---|---|---|---|
| Component | A | B | C | D |
| Dimethicone crosspolymer (DC 9045) | 26.000 | 26.000 | 26.000 | 26.000 |
| Glycerin | 10.000 | 10.000 | 10.000 | 10.000 |
| Parsol MCX (EthylhexylMethoxyCinnamate) | 6.000 | 6.000 | 6.000 | 6.000 |
| Zinc Oxide Powder | 2.000 | 2.000 | 2.000 | 2.000 |
| PEG-10 Dimethicone | 1.320 | 1.320 | 1.320 | 1.320 |
| Caprylic/Capric Triglycerides | 4.710 | 3.710 | 2.710 | 1.710 |
| (Cyclopentasiloxane (DC245) | 0.810 | 0.810 | 0.810 | 0.810 |
| Coated Mica (Timiron MP-111) | 0.500 | 0.500 | 0.500 | 0.500 |
| Bentone V CG | 0.270 | 0.270 | 0.270 | 0.270 |
| Glydant Plus ® | 0.200 | 0.200 | 0.200 | 0.200 |
| Disodium EDTA | 0.050 | 0.050 | 0.050 | 0.050 |
| Conjugated Linoleic Acid* | 0.000 | 1.000 | 2.000 | 3.000 |
| Water | 48.140 | 48.140 | 48.140 | 48.140 |

*Clarinol ® A-80: 36.9% CLA c9, t11 and 38.1% CLA t10, c12.

Protocol For Expert Facial Evaluation Panel

The Expert Panel is constituted from a group of women between ages 30 and 52. A multi-racial panel is selected. A sufficient number of subjects are recruited for each study to insure up to 40 subjects complete the study. They are trained to recognize facial conditions such as blemishes, color, discrete pigmentation, discrete features, lines and texture. These features contribute to the appearance of the face over different areas (i.e. forehead, sides and under the eye, upper cheek/cheek bone, lower cheek/jowl/side of mouth, nose, under nose, upper lip and chin). Initial training for the evaluation of these facial conditions involved to qualify an expert panel includes the requirement to look at themselves, at photographs, and at each other. Open discussions regarding their observations are required to occur at every stage.

Results

The study herein reported required panelists to evaluate two formulas applied to left and right sides of the face, respectively. Compositions A and B were evaluated as a set 1, each on half of a panel face. Likewise, compositions A and C were compared under set 2; compositions A and D were compared under set 3. These sets and results are reported in the Table below.

| Formula | Radiance Improvement Score | Improvement Change |
| --- | --- | --- |
| Set 1 | | |
| A (0% CLA) | 3.46 | — |
| B (1% CLA) | 4.96 | +1.50 |
| Set 2 | | |
| A (0% CLA) | 4.31 | — |
| C (2% CLA) | 3.44 | −0.87 |
| Set 3 | | |
| A (0% CLA) | 2.56 | — |
| D (3% CLA) | 2.39 | −0.17 |

Values for the base formula without CLA are given a Radiance Improvement Score relative to a totally untreated (with base formula) facial evaluation. The "improvement change" score in the above Table reflects the value improvement of the base formula over that wherein the base formula contains a particular percentage of CLA. The data indicates that at 1% CLA (composition B) there is a significant improvement change for Radiance. This improvement is not observed in formulas with higher levels of CLA (as seen in the scores for compositions C and D). This means that Radiance can be improved by the addition of a defined concentration level of CLA. Amounts beyond about 1.5% CLA provide no improvement, and in fact are less effective.

EXAMPLE XII

Experiments herein reported evaluated the effect of CLA in an oil continuous emulsion relative to a water continuous emulsion.

Comparative testing was performed in an Expert Facial Evaluation study. With minor differences, the protocol was identical to that reported in Example XI. Other than the samples tested, the only significant difference was that 14 panelists were utilized for this particular study. The two formulas evaluated are reported in the Table below.

| | Composition (Weight %) | |
| --- | --- | --- |
| Component | E | F |
| Dimethicone crosspolymer (DC 9045) | 20.000 | 20.000 |
| Glycerin | 9.000 | 9.000 |
| Parsol MCX (EthylhexylMethoxy Cinnamate) | 6.000 | 6.000 |
| Zinc Oxide Powder | 2.100 | 2.100 |
| Polysorbate 40 | 1.620 | 1.620 |
| Cetyl Alcohol | 1.550 | 1.550 |
| Silicone Fluid 200/50 cts | 1.000 | 1.000 |
| Coated Mica (Timiron MP-111) | 1.000 | 1.000 |
| Aristoflex AVC ® | 0.800 | 0.800 |
| Glycerol Monostearate | 0.780 | 0.780 |
| Polymethylmethacrylate Beads | 0.500 | 0.500 |
| DC 5225 C (Dimethicone Copolyol) | 0.500 | 0.500 |

-continued

| | Composition (Weight %) | |
| --- | --- | --- |
| Component | E | F |
| Phenoxyethanol | 0.400 | 0.400 |
| Fragrance | 0.300 | 0.300 |
| Methylparaben | 0.200 | 0.200 |
| Propyl Paraben | 0.100 | 0.100 |
| Glycacil L ® | 0.100 | 0.100 |
| Disodium EDTA | 0.050 | 0.050 |
| Conjugated Linoleic Acid* | 0.000 | 1.000 |
| Water | 54.000 | 53.000 |

*Clarinol ® A-80: 36.9% CLA c9, t11 and 38.1% CLA t10, c12.

Results of the panel study are reported in the Table below.

| Formula | Radiance Improvement Score | Improvement Change |
| --- | --- | --- |
| E (0% CLA) | 5.83 | — |
| F (1% CLA) | 5.46 | −0.37 |

The difference in the Radiance Improvement Score (over a baseline of untreated skin) demonstrates significant improvement was achieved with both sample E and F. However, Sample F with 1% CLA did not exhibit a better score than the 0% CLA Sample E. This contrasts to the results with the water-in-oil emulsions of Example XI. The 1% CLA formulated Sample B relative to 0% CLA Sample A exhibited an Improvement Change of 1.50. Thus, CLA has a much greater effect in oil continuous phase emulsions that in water continuous phase emulsions.

What is claimed is:

1. A cosmetic composition which is a water-in-oil emulsion comprising:
   (i) from about 0.1 to about 30% by weight of a water-in-oil emulsifying silicone surfactant;
   (ii) from about 0.01 to about 30% by weight of a crosslinked silicone elastomer; and
   (iii) from 0.2 to 1.5% of a conjugated linoleic acid.

2. The composition according to claim 1 wherein the water-in-oil surfactant is a silicone copolyol.

3. The composition according to claim 1 wherein the conjugated linoleic acid is present in an amount from 0.5 to 1.2% by weight of the composition.

4. The composition according to claim 1 wherein the conjugated linoleic acid consists essentially of at least 30% by weight of total conjugated linoleic acid present in the composition of a mixture of cis-9, trans-11 and trans-10, cis-12 linoleic acids.

5. The composition according to claim 4 wherein the conjugated linoleic acid consists essentially of at least 40% by weight of total conjugated linoleic acid present in the composition of a mixture of cis-9, trans-11 and trans-10, cis-12 linoleic acids.

6. The composition according to claim 1 wherein the silicone elastomer is formed from siloxane polymers with at least two free vinyl groups reacting with Si—H linkages on a polysiloxane backbone.

7. The composition according to claim 1 wherein the silicone elastomer is selected from the group consisting of dimethicone/vinyl dimethicone crosspolymer, dimethicone crosspolymer and polysilicone-11.

8. A method for enhancing facial radiance comprising applying to a face a cosmetic composition which is a water-in-oil emulsion comprising:
(i) from about 0.1 to about 30% by weight of a water-in-oil emulsifying silicone surfactant;
(ii) from about 0.01 to about 30% by weight of a crosslinked silicone elastomer; and
(iii) from 0.2 to 1.5% of a conjugated linoleic acid.

* * * * *

UNITED STATES PATENT AND TRADEMARK OFFICE
CERTIFICATE OF CORRECTION

| | | |
|---|---|---|
| PATENT NO. | : 7,175,836 B1 | Page 1 of 1 |
| APPLICATION NO. | : 11/318132 | |
| DATED | : February 13, 2007 | |
| INVENTOR(S) | : Hart et al. | |

It is certified that error appears in the above-identified patent and that said Letters Patent is hereby corrected as shown below:

On the title page

Item 73

Conopco, Inc., Englewood Cliffs, NJ    should read

Conopco, Inc. d/b/a Unilever, Englewood Cliffs, NJ

Signed and Sealed this

Seventeenth Day of April, 2007

JON W. DUDAS
*Director of the United States Patent and Trademark Office*